(12) United States Patent
Aoki et al.

(10) Patent No.: US 10,872,414 B2
(45) Date of Patent: Dec. 22, 2020

(54) INFORMATION PROCESSING APPARATUS, OBSERVATION SYSTEM, OBSERVATION METHOD, AND PROGRAM

(71) Applicant: Sony Corporation, Tokyo (JP)

(72) Inventors: Suguru Aoki, Tokyo (JP); Takeshi Ohashi, Kanagawa (JP); Naofumi Matsui, Kanagawa (JP); Tomoya Onuma, Shizuoka (JP)

(73) Assignee: Sony Corporation, Tokyo (JP)

( * ) Notice: Subject to any disclaimer, the term of this patent is extended or adjusted under 35 U.S.C. 154(b) by 95 days.

(21) Appl. No.: 16/307,662

(22) PCT Filed: May 18, 2017

(86) PCT No.: PCT/JP2017/018654
§ 371 (c)(1),
(2) Date: Dec. 6, 2018

(87) PCT Pub. No.: WO2017/217180
PCT Pub. Date: Dec. 21, 2017

(65) Prior Publication Data
US 2019/0220979 A1    Jul. 18, 2019

(30) Foreign Application Priority Data
Jun. 15, 2016  (JP) ................. 2016-119214

(51) Int. Cl.
*G06T 7/00* (2017.01)
*G01N 21/17* (2006.01)
(Continued)

(52) U.S. Cl.
CPC ........... *G06T 7/0016* (2013.01); *C12M 21/06* (2013.01); *C12M 41/36* (2013.01); *C12M 41/48* (2013.01);
(Continued)

(58) Field of Classification Search
CPC .................... G06T 7/0016; G06T 1/00; G06T 2207/30024; G06T 2207/10136;
(Continued)

(56) References Cited

U.S. PATENT DOCUMENTS 5,989,835 A * 11/1999 Dunlay ............... G02B 21/365
435/288.3
2003/0185422 A1* 10/2003 Taniguchi ............. A01K 45/00
382/110
(Continued)

FOREIGN PATENT DOCUMENTS

EP    2 615 460 A1    7/2013
EP    3 150 693 A1    4/2017
(Continued)

OTHER PUBLICATIONS

International Search Report and Written Opinion and English translation thereof dated Aug. 15, 2017 in connection with International Application No. PCT/JP2017/018654.
(Continued)

*Primary Examiner* — Nimesh Patel
(74) *Attorney, Agent, or Firm* — Wolf, Greenfield & Sacks, P.C.

(57) ABSTRACT

An information processing apparatus according to an embodiment of the present technology includes a control unit. The control unit detects, on a basis of an optical image of a cell in culture captured at a first imaging interval, whether there is a change in a state of the cell, and switches, when detecting the change in the state, an imaging mode from the first imaging interval to a second imaging interval shorter than the first imaging interval.

8 Claims, 14 Drawing Sheets

(51) Int. Cl.
*G06T 1/00* (2006.01)
*C12M 3/00* (2006.01)
*C12M 1/34* (2006.01)
*C12M 1/36* (2006.01)
*H04N 13/261* (2018.01)
*G01J 5/02* (2006.01)
*G01J 5/00* (2006.01)

(52) U.S. Cl.
CPC .............. *G01J 5/025* (2013.01); *G01N 21/17* (2013.01); *G06T 1/00* (2013.01); *H04N 13/261* (2018.05); *G01J 2005/0077* (2013.01); *G06T 2207/30024* (2013.01)

(58) Field of Classification Search
CPC ..... G06T 7/0012; C12M 41/48; C12M 41/36; C12M 21/06; G01N 21/17; G01N 33/085; G01N 15/147; G01N 29/0654; G01N 15/1463; G01N 23/04; G01N 33/08; G01N 9/36; G01J 5/025; G01J 2005/0077; H04N 13/261; A01K 43/06; A01K 43/04; A01K 45/00; A01K 45/007; A01K 2217/203; A01K 2217/206; A01K 2217/30; A01K 2267/035; A01K 2267/0393; A01K 67/0275; A01K 43/08
See application file for complete search history.

(56) References Cited

U.S. PATENT DOCUMENTS

| 2010/0195877 A1* | 8/2010 | Oonishi | C12M 21/06 382/128 |
| 2010/0208960 A1* | 8/2010 | Kiyota | C12M 41/48 382/128 |
| 2011/0092762 A1 | 4/2011 | Wong et al. | |
| 2014/0206931 A1* | 7/2014 | Zernicka-Goetz | G01N 33/4833 600/34 |
| 2015/0226654 A1* | 8/2015 | de Ketelaere | G01B 11/16 702/43 |
| 2015/0268227 A1* | 9/2015 | Tan | G06T 7/0016 435/29 |
| 2016/0161394 A1* | 6/2016 | Matsubara | H04N 5/2353 382/133 |
| 2016/0369223 A1* | 12/2016 | Matsumoto | G02B 21/244 |
| 2017/0073630 A1 | 3/2017 | Matsubara | |
| 2019/0331905 A1* | 10/2019 | Shinoda | G06T 7/80 |

FOREIGN PATENT DOCUMENTS

| JP | 2010-181402 A | 8/2010 |
| JP | 2011-017620 A | 1/2011 |
| JP | 2012-095627 A | 5/2012 |
| JP | 2013-502233 A | 1/2013 |
| JP | 2015-223174 A | 12/2015 |
| WO | WO 2011/025736 A1 | 3/2011 |

OTHER PUBLICATIONS

International Preliminary Report on Patentability and English translation thereof dated Dec. 27, 2018 in connection with International Application No. PCT/JP2017/018654.
Extended European Search Report dated Jun. 5, 2019 in connection with European Application No. 17813083.7.

\* cited by examiner

INFORMATION PROCESSING APPARATUS, OBSERVATION SYSTEM, OBSERVATION METHOD, AND PROGRAM

CROSS-REFERENCE TO RELATED APPLICATIONS

This application claims the benefit under 35 U.S.C. § 371 as a U.S. National Stage Entry of International Application No. PCT/JP2017/018654, filed in the Japanese Patent Office as a Receiving Office on May 18, 2017, which claims priority to Japanese Patent Application Number JP2016-119214, filed in the Japanese Patent Office on Jun. 15, 2016, each of which is hereby incorporated by reference in its entirety.

TECHNICAL FIELD

The present technology relates to an information processing apparatus, an observation system, an observation method, and a program that observe a cell in culture, for example.

BACKGROUND ART

In recent years, in order to analyze and evaluate a cultured biological cell or biological tissue in the livestock field, the regenerative medicine field, and the like, an apparatus that sequentially acquires a time-series image of the biological cell or biological tissue, and analyzes and evaluates the time-series image has been developed.

For example, Patent Literature 1 discloses a fertilized egg quality evaluation support method in which time-series images of a fertilized egg are acquired, and the growth state of the fertilized egg is observed and evaluated on the basis of the difference in pixel value between the time-series images.

CITATION LIST

Patent Literature

Patent Literature 1: Japanese Patent Application Laid-open No. 2010-181402

DISCLOSURE OF INVENTION

Technical Problem

However, as can be seen from that fact that the cell cycle can be divided into a mitosis phase and an interphase, the degree of state change of the cell is not constant. Therefore, in the case where a fertilized egg is imaged at constant intervals throughout the entire period as in the fertilized egg quality evaluation support method described in Patent Literature 1, there is a risk of missing an important imaging timing to image the fertilized egg in the mitosis phase in which the state change is remarkable, and the like. Meanwhile, continuing to performing imaging at short intervals according to the mitosis phase is practically difficult, because not only the image capacity becomes enormous but also it takes a huge amount of time to analyze the image.

In view of the circumstances as described above, it is an object of the present technology to provide an information processing apparatus, an observation system, an observation method, and a program that are capable of avoiding missing an important imaging timing.

Solution to Problem

An information processing apparatus according to an embodiment of the present technology includes a control unit.

The control unit detects, on a basis of an optical image of a cell in culture captured at a first imaging interval, whether there is a change in a state of the cell, and switches, when detecting the change in the state, an imaging mode from the first imaging interval to a second imaging interval shorter than the first imaging interval.

Accordingly, it is possible to avoid missing an important imaging timing.

The control unit may be configured to detect whether there is a change in the state of the cell from a thermal image of the cell in culture.

Accordingly, it is possible to more precisely switch the imaging interval while reducing damage on the cell.

The optical image may be a three-dimensional image obtained from a plurality of optical images captured from multiple viewpoints, and the control unit may be configured to detect, depending on a change in a feature amount of the cell quantified on a basis of information of the three-dimensional image, whether there is a change in the state of the cell.

Accordingly, it is possible to more precisely switch the imaging interval, and avoid missing an important imaging timing.

The cell may be a fertilized egg, and the feature amount of the cell may be a volume, a surface area, a sphericity, and a degree of a surface irregularity of the fertilized egg, and a uniformity of cleavage.

An observation system according to an embodiment of the present technology includes a cell culture vessel; an imaging unit; and a control unit.

The cell culture vessel cultures a cell.

The imaging unit includes an optical image capturing unit acquiring, at a first interval, an optical image of the cell in culture.

The control unit detects, on a basis of an image of the cell in culture captured at the first imaging interval, whether there is a change in a state of the cell, and switches, when detecting the change in the state, an imaging mode from the first imaging interval to a second imaging interval shorter than the first imaging interval.

The imaging unit may include a thermal image capturing unit sequentially acquiring a thermal image of the cell in culture, and the control unit may detect, on a basis of the thermal image captured by the thermal image capturing unit, whether there is a change in the state of the cell.

The optical image capturing unit may acquire multi-viewpoint optical images of the cell.

The observation system may further include an optical image database unit and a three-dimensional reconstruction unit.

The optical image database unit stores the multi-viewpoint optical images.

The three-dimensional reconstruction unit acquires the multi-viewpoint optical images from the optical image database unit, and three-dimensionally reconstructs the multi-viewpoint optical images.

The control unit may detect, on a basis of the three-dimensionally reconstructed multi-viewpoint optical images, whether there is a change in the state of the cell.

An observation method according to an embodiment of the present technology includes: detecting, on a basis of an optical image of a cell in culture captured at a first imaging interval, whether there is a change in a state of the cell; and switching, when detecting the change in the state, an imaging mode from the first imaging interval to a second imaging interval shorter than the first imaging interval.

A program according to an embodiment of the present technology causes an information processing apparatus to execute the steps of: detecting, on a basis of an optical image of a cell in culture captured at a first imaging interval, whether there is a change in a state of the cell; and switching, when detecting the change in the state, an imaging mode from the first imaging interval to a second imaging interval shorter than the first imaging interval.

Advantageous Effects of Invention

As described above, according to the present technology, it is possible to avoid missing an important imaging timing.

It should be noted that the effect described here is not necessarily limitative and may be any effect described in the present disclosure.

MODE(S) FOR CARRYING OUT THE INVENTION

Hereinafter, embodiments of the present technology will be described with reference to the drawings. Note that descriptions will be made in the following order.

First Embodiment

[Overview of Observation System]

Figure 1:
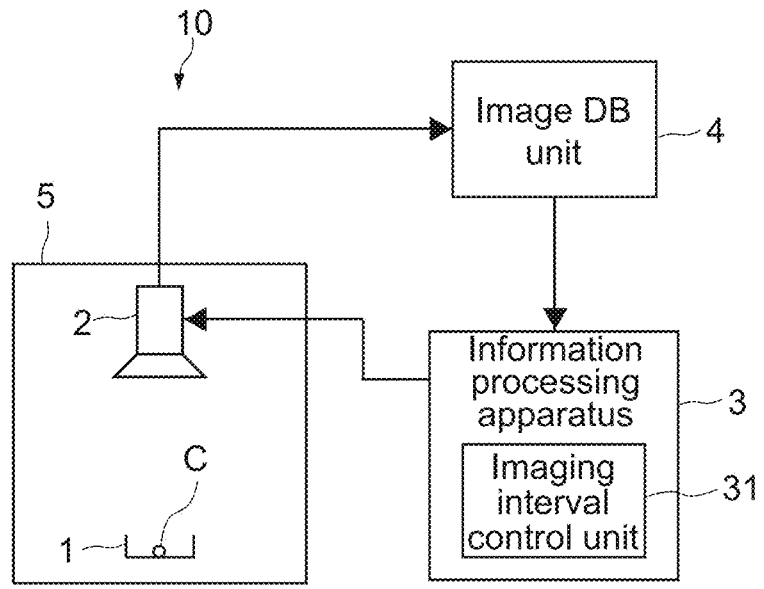
FIG. 1 is a block diagram showing a schematic configuration of an information processing apparatus according to an embodiment of the present technology.
Figure 2:
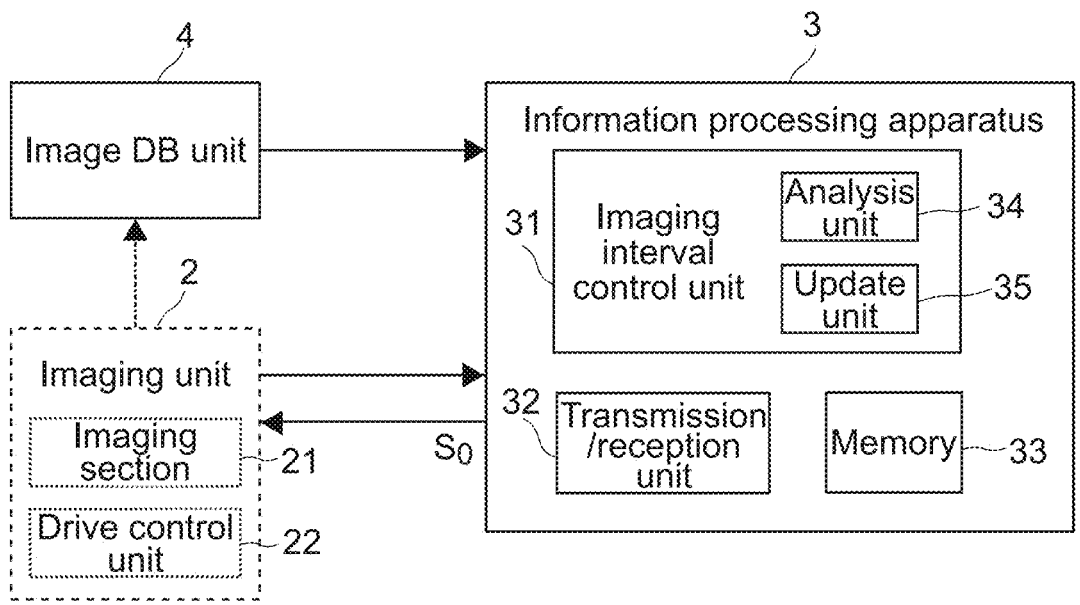
FIG. 2 is a block diagram showing a main part of the observation system.

FIG. 1 is a block diagram showing an observation system 10 according to an embodiment of the present invention. FIG. 2 is a block diagram showing a main part of the observation system 10.

The observation system 10 includes a culture vessel 1, an imaging section 2, and an information processing apparatus 3.

The culture vessel 1 is configured to be capable of housing a culture solution and one or more cells C, and is transparent enough to image the cell C from the outside. The shape of the culture vessel 1 is not particularly limited, and typically has a flat plate shape such as a petri dish. The number of the culture vessels 1 is not particularly limited, and may be one or more.

As used herein, "cell" (singular) conceptually includes at least a single cell and an aggregate of a plurality of cells. Examples of the "cell" cultured in the culture vessel 1 include, but not particularly limited to, an unfertilized egg cell (ovum), a fertilized egg, an embryo, and the like of an organism in the livestock field and the like, and a biological sample taken out of a living body, such as a stem cell, an immune cell, a cancer cell, and the like in the fields of regenerative medicine, pathological biology, and the like.

The imaging unit 2 images the cell C housed in the culture vessel 1 at a predetermined imaging interval to acquire an optical image of the cell C. The imaging unit 2 includes a solid-state image sensor (imaging section 21) such as a CMOS (Complementary Metal Oxide Semiconductor) and a CCD (Charge Coupled Device), a drive control unit 22 that controls driving of the imaging section 21. The imaging unit 2 typically includes a visible light camera and may include a built-in strobe. The imaging unit 2 may include a near-infrared camera instead of or in addition to the visible light camera.

The culture vessel 1 and the imaging unit 2 are supported by an observation table 5 that keeps the relative distance between them constant. The imaging unit 2 is typically fixed at a position facing the cell C in the culture vessel 1. However, the imaging unit 2 may be installed so as to be movable relative to the culture vessel 1. The number of imaging units 2 is not particularly limited, and may be one or more. In the case where a plurality of imaging units 2 are installed, it is possible to observe the cell C from multiple viewpoints, and combines the multi-viewpoint images to acquire a three-dimensional image.

The information processing apparatus 3 includes an imaging interval control unit 31 that controls the imaging interval of the imaging unit 2. The information processing apparatus 3 acquires, from an image DB (database) unit 4, an optical image of the cell C in culture captured at a first imaging interval. The information processing apparatus 3 determines, on the basis of the optical image of the cell C, whether there is a predetermined change in the state of the cell C, and generates, when detecting the change in the state, a control signal $S_0$ for switching the imaging interval from the first imaging interval to a second imaging interval shorter than the first imaging interval, by the imaging interval control unit 31. The information processing apparatus 3 outputs the control signal $S_0$ to the imaging unit 2.

The imaging unit 2 acquires, on the basis of the control signal $S_0$ regarding the imaging interval output from the information processing apparatus 3, the optical image of the cell C at a predetermined imaging interval. The imaging unit 2 transmits the optical image of the cell C captured at the interval to the image DB unit 4.

The image DB unit 4 stores the optical image of the cell C captured by the imaging unit 2, and transmits the optical image of the cell C to the information processing apparatus 3 in time series. The image DB unit 4 may include a general-purpose computer, or a cloud server connected to the imaging unit 2 and the information processing apparatus 3 via an Internet line.

[Information Processing Apparatus]

Next, details of the information processing apparatus 3 will be described. The information processing apparatus 3 includes the imaging interval control unit 31, a transmission/reception unit 32, and a memory 33.

The imaging interval control unit 31 includes an analysis unit 34 and an update unit 35. A program recorded in a ROM (Read Only Memory), which is an example of a non-transitory computer readable recording medium, is loaded into a RAM (Random Access Memory), and a CPU (Central Processing Unit) executes the program, thereby realizing the analysis unit 34 and the update unit 35.

The imaging interval control unit 31 is configured to be capable of selectively switching the imaging mode between the first imaging interval and the second imaging interval depending on the change in the state of the cell C. The second imaging interval is shorter than the first imaging interval. The first imaging interval and the second imaging interval are not particularly limited, and can be appropriately set depending on the type of the cell C, the type of the change in the state to be evaluated, the speed of the change in the state, and the like. For example, the first imaging interval can be set to several seconds to several tens of minutes, and the second imaging interval can be set to several tens milliseconds to several minutes. That is, in the second imaging mode, the imaging unit 2 may take a video of the cell C.

The analysis unit 14 is configured to analyze, on the basis of the time-series image of the cell C, the optical image of the cell C to detect whether there is a change in the state of the cell C. For example, by generating a difference image of two optical images of the cell C captured at different times, whether there is a change in the state of the cell C can be detected. Details thereof will be described later.

The update unit 15 generates a signal $S_0$ for switching the imaging interval between the first imaging interval and the second imaging interval depending on the analysis result by the analysis unit 14.

The transmission/reception unit 32 acquires the captured optical image of the cell C from the image DB unit 4. The transmission/reception unit 32 may be configured to directly acquire the optical image of the cell C from the imaging unit 2. Further, the transmission/reception unit 32 transmits the signal $S_0$ for controlling the imaging interval to the imaging unit 2. The transmission/reception unit 32 includes, for example, a communication circuit and an antenna, and constitutes an interface for communicating with the imaging unit 2 and the image DB unit 4. Note that the communication performed by the transmission/reception unit 32 may be wireless or wired. The wireless communication may be communication using an electromagnetic wave (including an infrared ray) or communication using an electric field.

The memory 33 includes a ROM, a RAM, and the like, and stores an algorithm for determining whether there is a change in the state of the cell, a program for controlling the imaging interval, a program for performing correction processing on image data, an image of the cell C acquired from the image DB unit 4 (imaging unit 2), and the like. Further, various parameters for executing the programs, data, and the like may be stored in the memory 33.

[Operation Example of Observation System]

Figure 3:
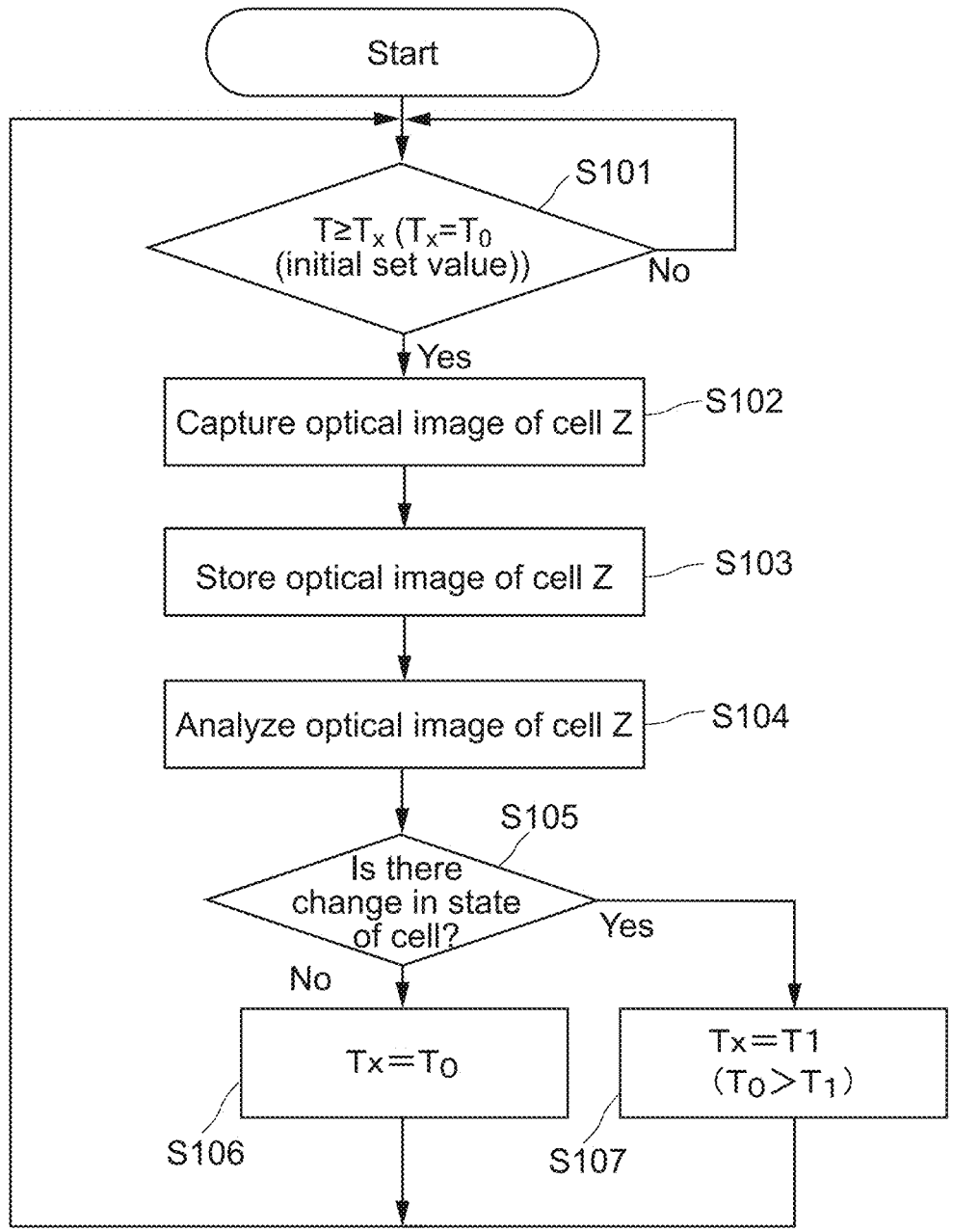
FIG. 3 is a flowchart showing an operation example of the observation system.

Hereinafter, as shown in FIG. 3, an operation example of the observation system 10 according to this embodiment will be described.

The observation system 10 according to this embodiment acquires an optical image of the cell C (S101, 102) every time a predetermined imaging interval Tx elapses, stores the captured optical image of the cell C in the image DB unit 4 (S103), and analyzes the stored optical image of the cell C by the information processing apparatus 3 (S104). The observation system 10 detects whether there is a change in the state of the cell C by the above-mentioned analysis result (S105), and changes the above-mentioned imaging interval Tx depending on the detection result (S106, 107).

Here, in the case where the change in the state of the cell C is not detected (No in S105), the imaging interval control unit 31 maintains the imaging interval $T_0$ (initial set value) (S106). Meanwhile, in the case where the change in the state of the cell is detected (Yes in S105), the imaging interval control unit 31 switches the imaging interval to $T_1$ shorter than $T_0$ (S107). The imaging unit 2 performs imaging at the imaging interval $T_1$ (S101, S102).

Figure 4:
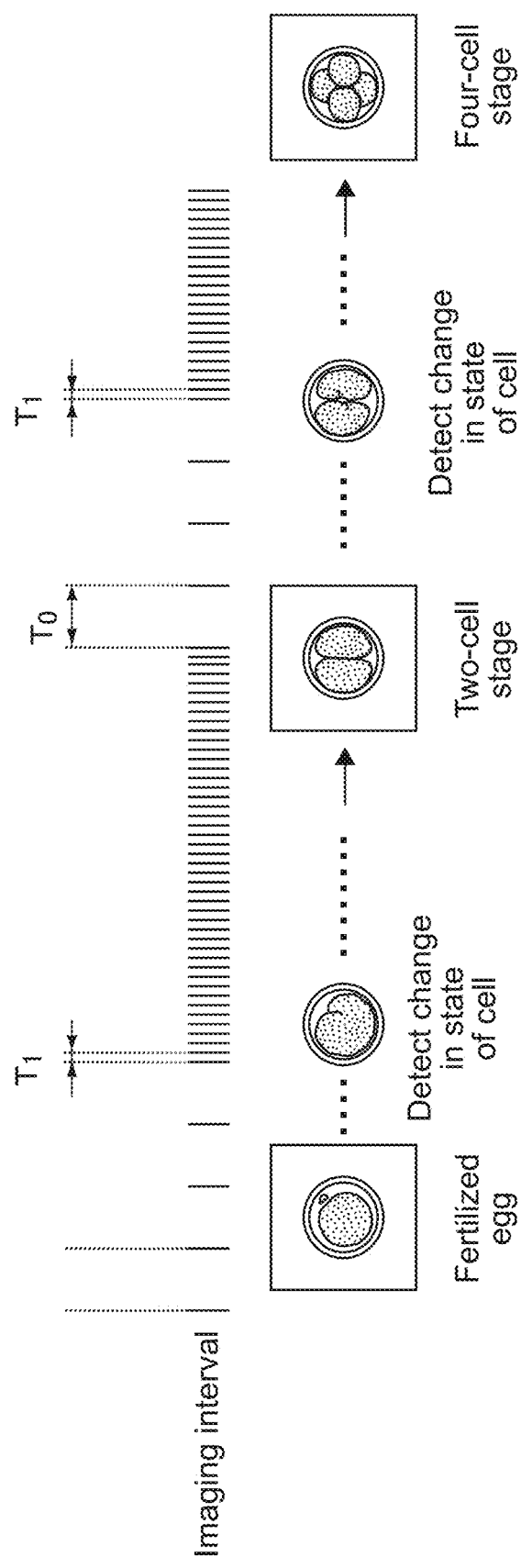
FIG. 4 is a diagram showing a specific example of the operation of switching an imaging interval by an imaging unit 21 of the observation system.

FIG. 4 is a schematic diagram showing an example of the change in the state of a fertilized egg (cell C). In the case where the change in the state of the fertilized egg is not detected, the imaging unit 2 images the fertilized egg at the imaging interval $T_0$. In the case where a change of the fertilized egg to the two-cell stage is detected, the imaging unit 2 images the fertilized egg at the short imaging interval $T_1$. Next, in the case where the change in the two-cell stage is stopped (i.e., change in the state is not detected), the imaging unit 2 images the fertilized egg at the imaging interval $T_0$ again. Further, in the case where the change from the two-cell stage to the four-cell stage is detected, the imaging unit 2 performs imaging at the imaging interval $T_1$ again.

The flow of a typical operation is as follows. In the case where the change in the state of the cell is not detected, the imaging interval control unit 31 causes the imaging unit 2 to perform control to image the cell C at the imaging interval $T_0$. In the case where the change in the state of the cell C is detected, the imaging interval control unit 31 causes the imaging unit 2 to perform control to image the cell C at the imaging interval $T_1$ shorter than the imaging interval $T_0$. After that, in the case where the change in the state of the cell C is not detected, the imaging interval control unit 31 returns the imaging interval for the cell C from $T_1$ to $T_0$. Accordingly, it is possible to adaptively change the imaging interval depending on the growth stage of the cell, and perform imaging without missing an important timing related to evaluation of the cell.

The imaging interval is set to, for example, 5 min ($T_0$) in the resting phase before cell division, and 30 msec ($T_1$) in the case where the change in the state of the cell C is detected. Note that the imaging interval may be gradually switched depending on the change in the state of the cell.

In order to detect the change in the state where the cell C starts cell division, the imaging interval control unit 31 detects, for example, the change in the feature amount such as generation of a cell boundary surface or an inner cell mass, the increase in the surface area or volume of the cell, the change in the sphericity of the cell. By detecting them, it is possible to perform imaging at fine imaging intervals at an important timing where the cell C starts cell division.

[Description of Specific Operation Example of Imaging Interval Control Unit]

An example of the specific operation of the imaging interval control unit 31 according to this embodiment will be described.

The imaging interval control unit 31 (analysis unit 34) calculates, for example, a difference value of two optical images captured at different times, and determines whether or not the difference value is not less than a threshold value by comparing them. In the case where the difference value is not less than the threshold value, the analysis unit 34 regards the image change as large and detects (determines) that there is a change in the state of the cell C. The two optical images captured at different times specifically represent an optical image of the current cell and an optical image of the past cell (previous image or a plurality of predetermined images captured at the previous time and therebefore). By detecting a change with the optical image of the current cell, it is possible to switch the imaging interval in real time at an important timing where the cell division is started, and perform imaging. As the method of detecting the change in the state from the two optical images captured at different imaging times, in addition to the method of calculating the difference values of pixels of the optical images, optical images captured from a multiple viewpoints may be three-dimensionally reconstructed, and the change in the state may be detected on the basis of the change amount of the feature amount extracted from the obtained three-dimensional image as will be described later. The method of detecting the change in the state is not particularly limited.

Here, since the cell C in culture slightly rotates or moves in parallel in a culture vessel, the position and size of the cell image to be captured are changed in some cases. In order to solve this problem, the optical image of the cell C may be rotated, moved in parallel, or scaled to correct the position and size of the cell before calculating the difference between the two images. At this time, the determination is performed by adopting, for example, the smallest value of the difference between the corrected cell images. Accordingly, it is possible to more precisely detect the change in the state of the cell C. Note that the information processing apparatus according to this embodiment may separately include a CPU and memory for executing the above-mentioned correction processing.

CONCLUSION

The state of a cell is changed at different degrees depending on the type of the cell to be cultured, the growth stage of the cell, and the like. In the case where the cell is imaged at a constant interval as before, there is a risk of missing a timing to image the division related to evaluation of the cell in the mitosis phase in which the change in the state of the cell is remarkable. Meanwhile, in the case where imaging is performed at fine imaging intervals, the data amount of the image becomes enormous and it takes a huge amount of time to process the image. Meanwhile, according to this embodiment, it is possible to switch the imaging interval depending on the change in the state of the cell and perform imaging with high density at an important timing where the state of the cell is changed. Further, by performing imaging with high density only at an important timing and performing imaging with low density in a normal imaging mode, it is possible to reduce the capacity of the image to be stored or processed. Further, by not increasing the number of times of imaging more than necessary, it is possible to reduce damage on the cell due to irradiation light applied at the time of imaging.

Second Embodiment

Next, a second embodiment of the present technology will be described. Hereinafter, configurations that are different from those according to the first embodiment will be mainly described. The configurations similar to those according to the first embodiment will be denoted by similar reference symbols and a description thereof will be omitted or simplified.

An observation system 20 according to this embodiment is different from the first embodiment in that it includes an imaging unit 12 capable of acquiring multi-viewpoint images of the cell C. By observing the cell C from multiple viewpoints, it is possible to more precisely detect the change in the state of the cell C.

Configuration Example 1

Figure 5:
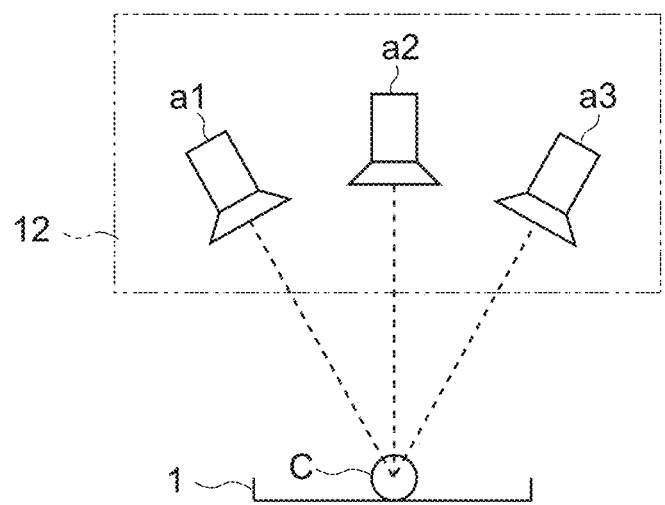
FIG. 5 is a diagram showing an example (configuration example 1) of a configuration of an optical imaging unit in the observation system.

The observation system 20 shown in FIG. 5 includes an imaging unit 12 that images, by a plurality of cameras a1 to a3, the cell C housed in the culture vessel 1 including a flat dish such as a petri dish. The cameras a1 to a3 may be arranged around the cell C in the circumferential direction along the surface of the cell C. Accordingly, it is possible to acquire multi-viewpoint images in which the upper hemisphere of the cell can be observed, and more precisely detect the change in the state of the cell. As will be described later, the multi-viewpoint images may be three-dimensionally reconstructed to form a three-dimensional image. The number of cameras to be arranged is not particularly limited. However, as the number of cameras is increased, an image of an occlusion area can be additionally provided, and it is possible to more precisely detect the change in the state.

The imaging interval control unit 31 (FIG. 2) may individually control the respective imaging intervals for the cameras a1 to a3, or may commonly control the imaging intervals for the cameras a1 to a3. For example, the imaging interval control unit 31 may control the imaging unit 12 so as to individually acquire the optical image of the cell C from the cameras a1 to a3 at the above-mentioned predetermined imaging interval, or may control the imaging unit 12 so as to switch the cameras a1 to a3 at the above-mentioned imaging interval to acquire the optical image of the cell C from the camera.

Configuration Example 2

Figure 6:
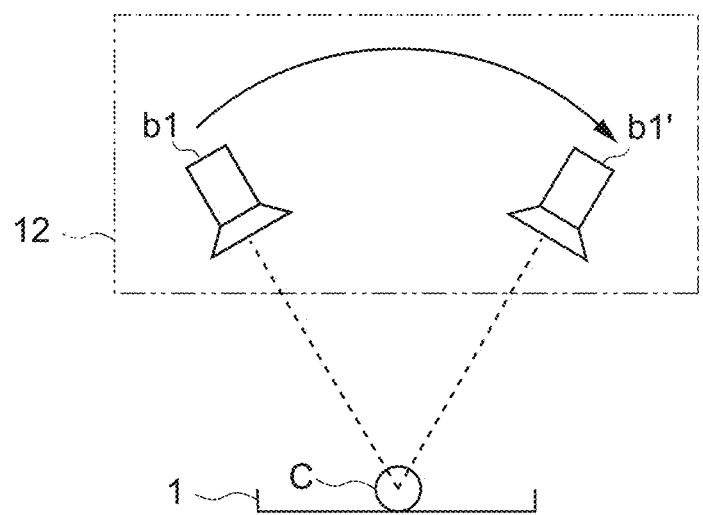
FIG. 6 is a diagram (configuration example 2) showing an example of the configuration of the optical imaging unit in the observation system.

The observation system 20 shown in FIG. 6 includes the imaging unit 12 that images, by a movable camera b1, the cell C housed in the culture vessel 1 including a flat dish such as a petri dish. The camera b1 is configured to be capable of moving around the cell C in the circumferential direction along the surface of the cell C to the position of the camera b1'. Accordingly, it is possible to acquire multi-viewpoint images of the upper hemisphere of the cell C similarly as described above. Further, since the number of cameras to be arranged can be reduced, it is also possible to reduce the size and cost of the apparatus.

Configuration Example 3

Figure 7:
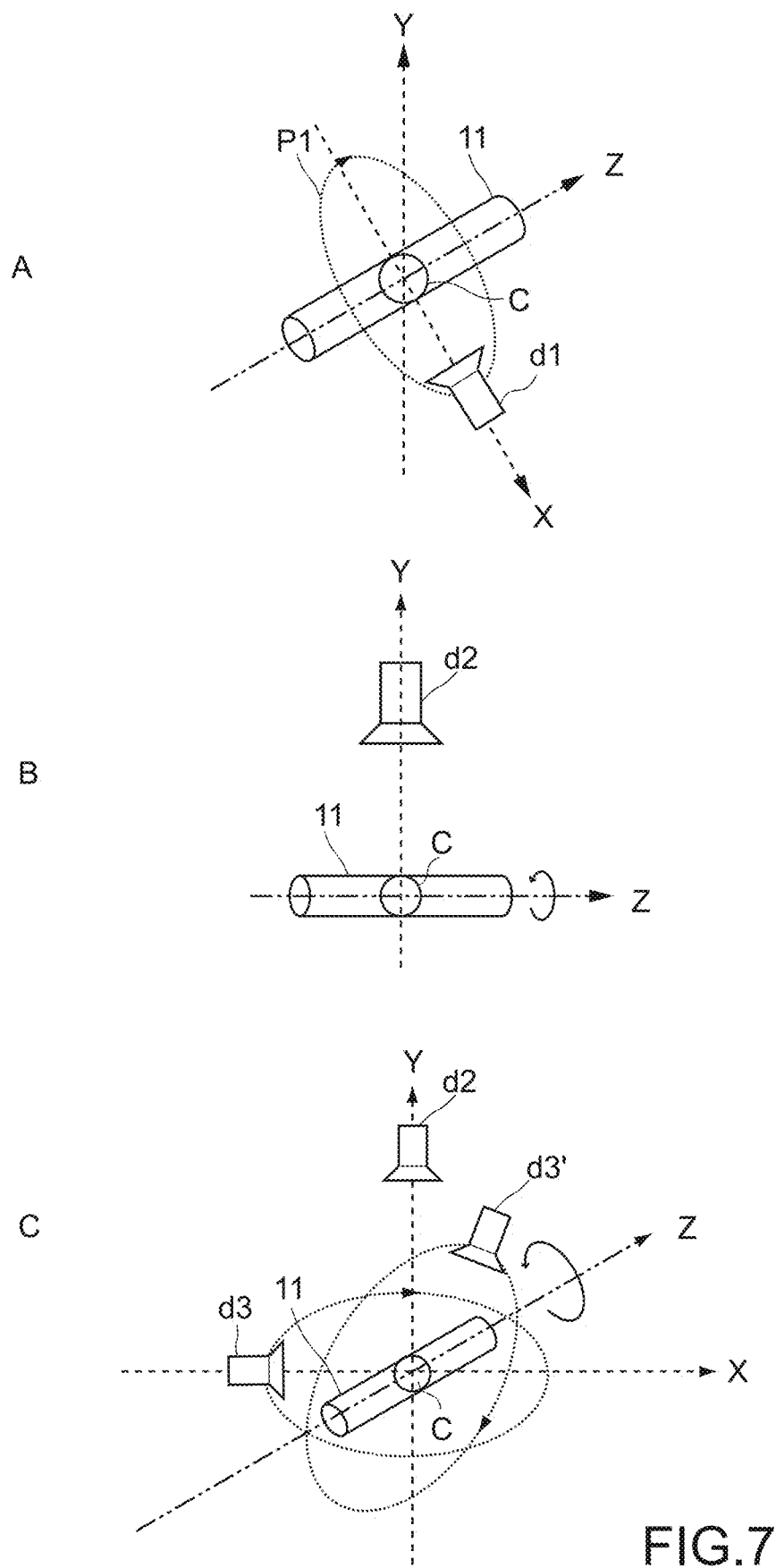
FIG. 7 is a diagram (configuration example 3) showing an example of configurations of the optical imaging unit and a culture vessel in the observation system.

In the observation system 20 shown in Part A of FIG. 7, a vessel housing the cell C includes a cylindrical vessel 11 formed of a circular tube having transparency, and a camera d1 is configured to be capable of moving so as to observe the cell C from an entire circumferential direction P1 of the side surface of the cylindrical vessel. Accordingly, it is possible to not only the image of the upper hemisphere of the cell C but also an image of the lower hemisphere of the cell C. That is, since the entire circumferential image of the cell C can be acquired, it is possible to more precisely detect the change in the state of the cell.

Configuration Example 3'

Meanwhile, in the observation system shown in Part B of FIG. 7, the cylindrical vessel 11 is configured to be capable of rotating in the circumferential direction (around the Z axis), and a camera d2 that images the side surface of the cylindrical vessel 11 is fixed at a predetermined position on the Y axis perpendicular to the Z axis. Accordingly, similarly to the configuration example 2, it is possible to acquire the entire circumferential image of the cell C. Further, since the number of cameras can be reduced and there is no need to provide space for moving the camera, it is possible to reduce the size and cost of the apparatus.

Configuration Example 3"

Further, in addition to the above-mentioned configuration example (Configuration Example 3'), in the observation system shown in Part C of FIG. 7, a camera d3 (d3') can be movably installed so as to be capable of imaging the cell C from the Z-axis direction of the cylindrical vessel 11. For example, as shown in the figure, the camera d3 (d3') circularly moves around the cell C in the X-Z plane (Y-Z plane). Accordingly, since an optical image can be acquired from all directions, it is possible to more precisely detect the change in the state of the cell and perform imaging at short imaging intervals at an important timing.

Configuration Example 4

Figure 8:
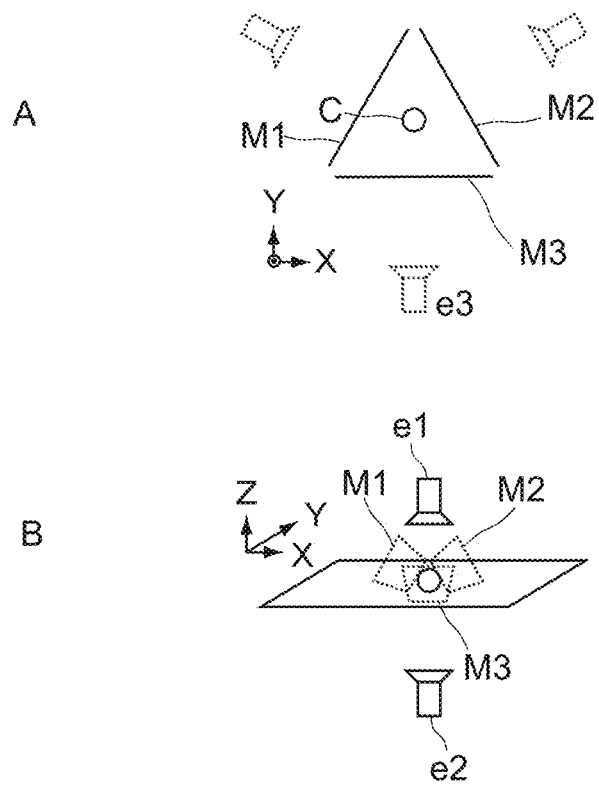
FIG. 8 is a diagram (configuration example 4) showing an example of the configuration of the optical imaging unit in the observation system.

The observation system 20 shown in Part A and Part B of FIG. 8 includes mirrors (M1 to M3) arranged at equal angular intervals so as to surround the cell C placed on the horizontal plane (X-Y surface). Then, as shown in Part B of FIG. 8, a camera e1 disposed above the cell C in the vertical direction may capture an image of the cell C and a reflection image of the mirrors (M1 to M3). Accordingly, it is possible to acquire an optical image captured from above the cell C in the vertical direction and an optical image captured from the circumferential direction around the cell C in the horizontal plane. Further, as will be described later, multi-viewpoint images may be three-dimensionally reconstructed to form a three-dimensional image. The number of mirrors to be arranged is not particularly limited. However, as the number of mirrors is increased, an image of an occlusion area can be additionally provided, and it is possible to more precisely detect the change in the state.

Further, as shown in Part B of FIG. 8, a camera e2 that images the cell C from below may be further disposed. Accordingly, since an optical image of the cell C in the lower visual field can be acquired, it is possible to acquire a cell image viewed from all directions.

Configuration Example 5

The observation system shown in FIG. 9 includes a culture vessel 12 housing a plurality of cells C1 to C3, and a plurality of cameras f1 to f3 arranged above the corresponding cells in the vertical direction, and the cameras f1 to f3 each have a viewing angle capable of simultaneously imaging not only the cell located immediately below but also the surrounding cells. As a result, for example, regarding the cell C2, it is possible to acquire not only a viewpoint image from the camera f2 (viewpoint F2) but also a viewpoint image from the camera f1 (viewpoint F12) and a viewpoint image from the camera f3 (viewpoint F32). Accordingly, it is possible to observe the respective cells C1 to C3 from multiple viewpoints. Further, it is possible to reduce the number of cameras to be arranged.

Figure 9:
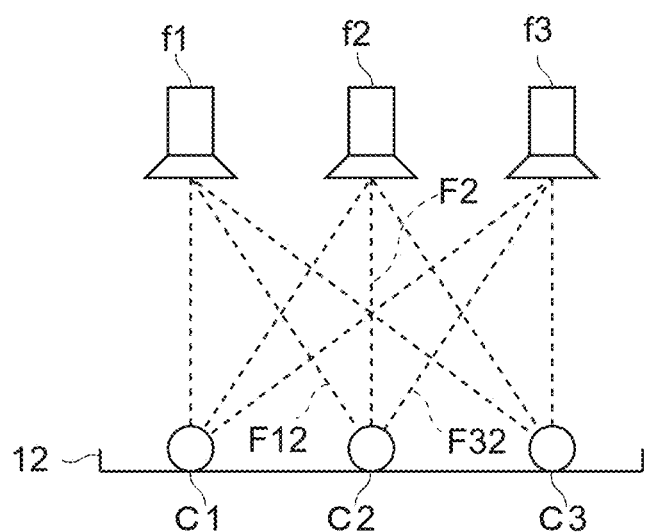
FIG. 9 is a diagram (configuration example 5) showing an example of the configuration of the optical imaging unit in the observation system.

Here, since the optical axes of the cameras f1 to f3 are parallel to each other in FIG. 9, for example, the position and appearance of the viewpoint image of the cell C1 captured by the camera f2 may differ depending on the difference in the optical axis. In this case, the image of the cell C1 captured by the camera f2 only needs to be converted into an image obtained by directing the optical axis of the camera f2 toward the cell C1. Accordingly, it is possible to observe one cell from a plurality of viewpoints without changing the position and orientation of each camera.

Figure 10:
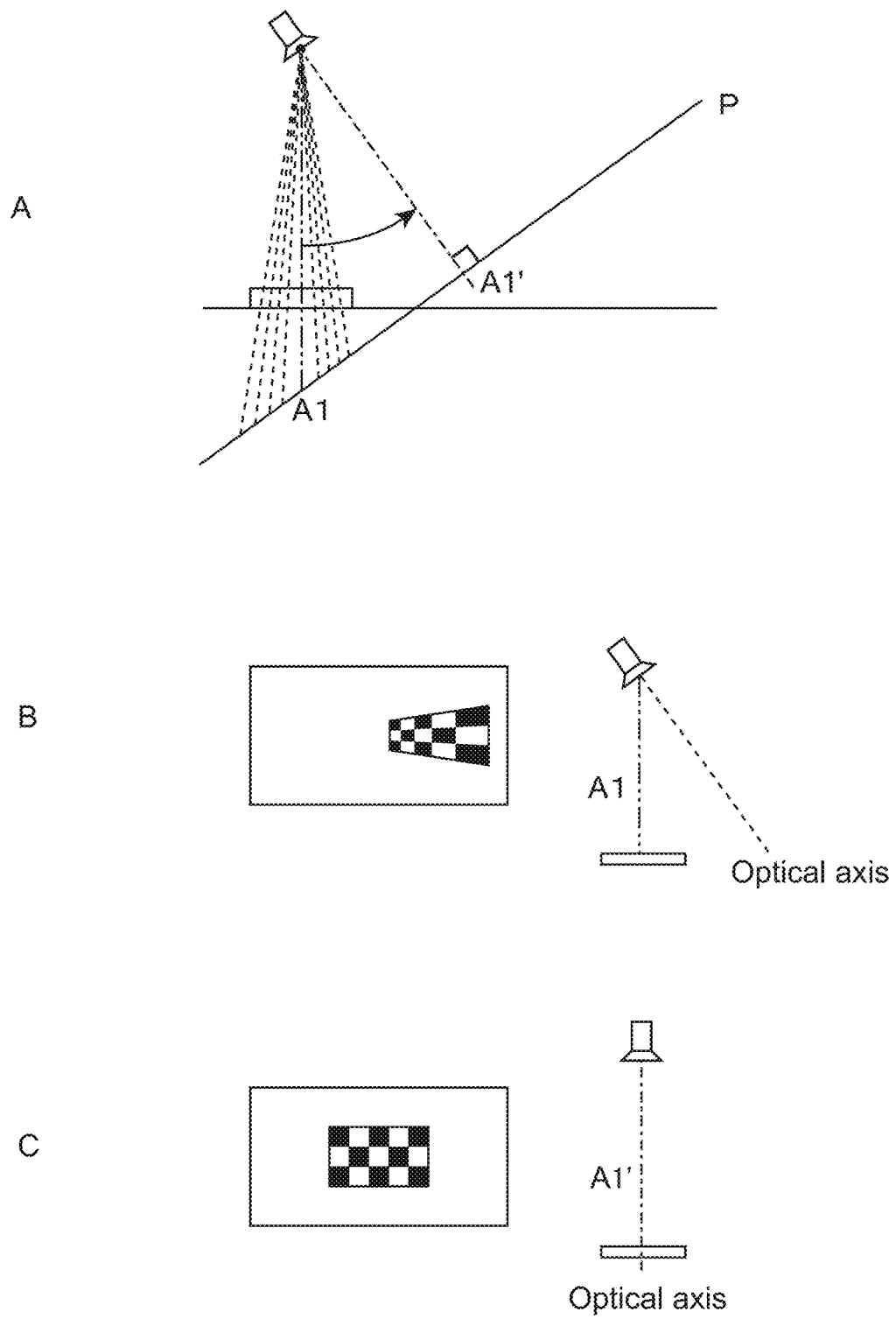
FIG. 10 is a diagram showing a general method of acquiring an image with a corrected optical axis.

The method of changing the optical axis of the camera is not particularly limited, and various methods can be adopted. For example, as shown in Part A of FIG. 10, by projecting the image with an optical axis A1 onto an image plane P perpendicular to an optical axis A1', it is possible to create an image in which the optical axis is converted from A1 to A1'. For example, in the case where a checkerboard is imaged, appearances of an image with the optical axis A1 and an image with the optical axis A1' obtained by the optical axis conversion differ as shown in Part B and Part C of FIG. 10.

Figure 11:
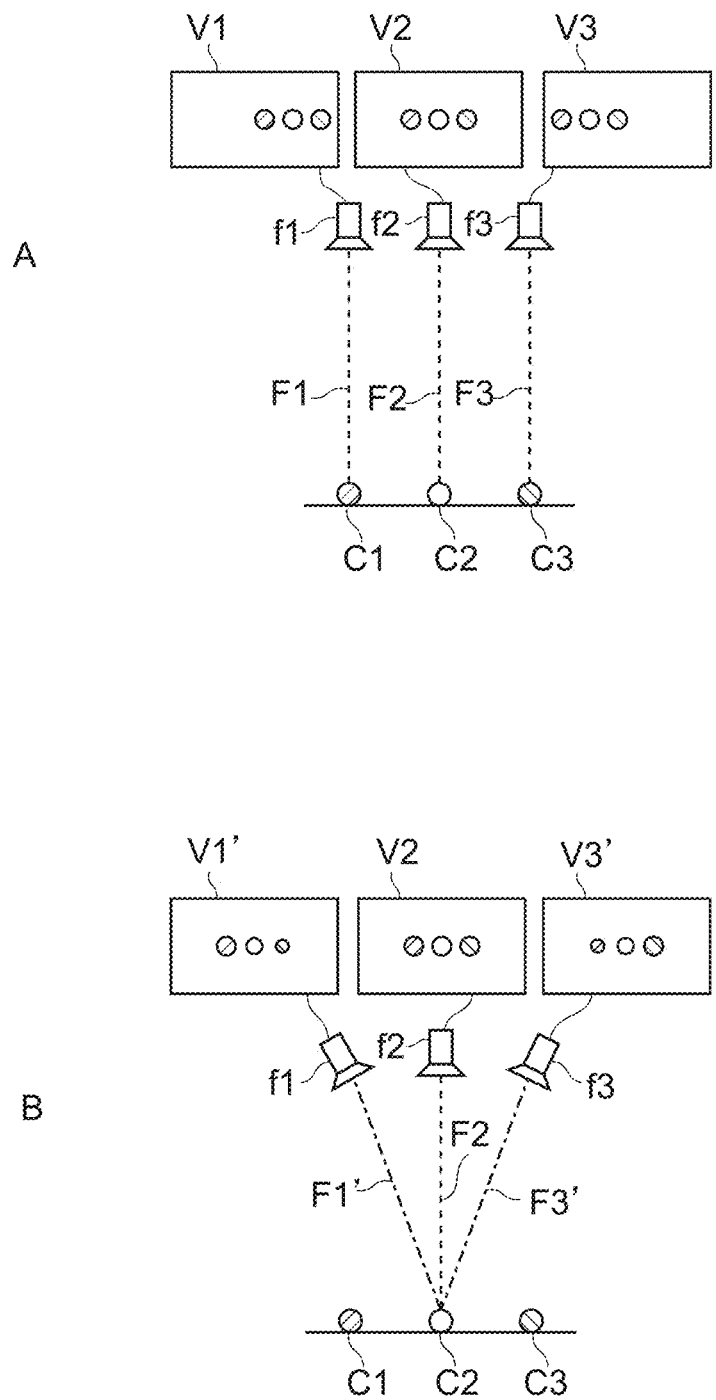
FIG. 11 is a diagram showing a method of acquiring the image with the corrected optical axis by the optical imaging unit (configuration example 1) in the observation system.

In this regard, as shown in Part A and Part B of FIG. 11, in the case of observing the cell C2 located at the center, images V1' and V3' obtained by respectively converting the optical axes F1 and F3 of the adjacent cameras f1 and f3 into optical axes F1' and F3' centered on the cell C2 are acquired. In the image obtained by the optical axis conversion, an object on the optical axis appears at the center of the image, an object far from the optical axis is small, and an object near the optical axis is large. By creating an image with the converted optical axis as described above and integrating cell images captured from a plurality of viewpoints, it is possible to more accurately detect the change in the state of the cell.

Further, as will be described later, images of two viewpoints may be acquired from a plurality of cameras, and three-dimensionally reconstructed by stereo matching. The image conversion processing method for camera stereo matching will be described later.

CONCLUSION

Regarding the change in the state of the cell due to the cell division, the boundary surface of the division or the like cannot be imaged depending on the imaging angle in some cases. Further, in the case of performing imaging from one viewpoint, there occurs a situation in which the part that it has been possible to image so far cannot be imaged due to the dynamic change such as rotational movement of the cell. In the configuration of this embodiment, by acquiring optical images of the cell from multiple viewpoints, it is possible to detect the change in the state of the cell without overlooking it. Therefore, it is possible to more precisely switch the imaging interval at an important timing in the growth process of the cell.

Third Embodiment

Figure 12:
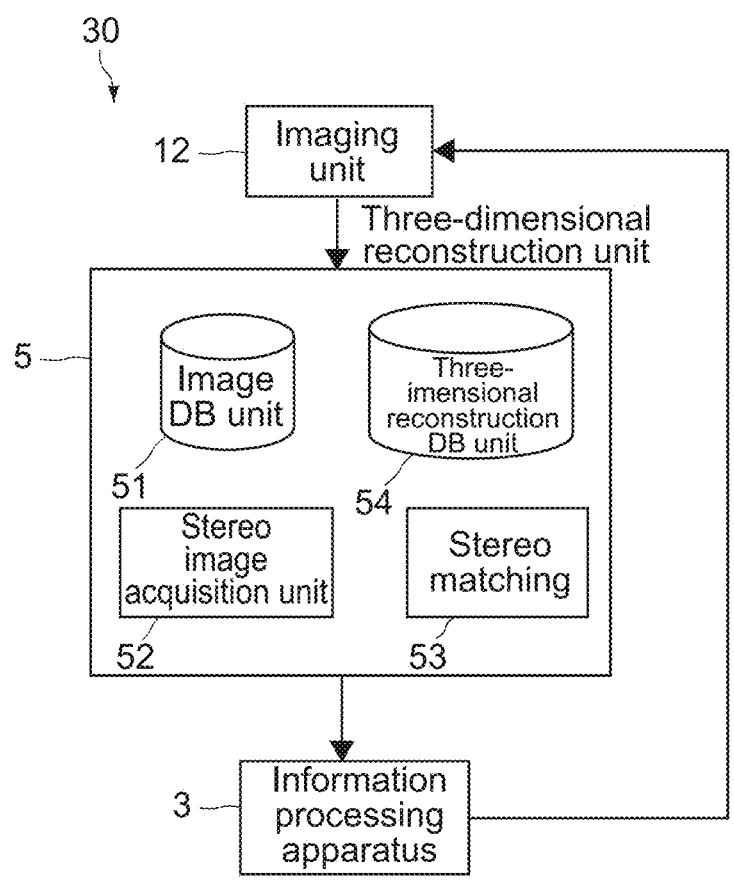
FIG. 12 is a block diagram showing a configuration of a three-dimensional reconstruction unit according to a third embodiment of the present technology.

Next, a third embodiment of the present technology will be described. FIG. 12 is a block diagram showing a configuration of an observation system 30 according to this embodiment. Hereinafter, configurations that are different from those according to the first and second embodiments will be mainly described. The configurations similar to those according to the first and second embodiments will be denoted by similar reference symbols and a description thereof will be omitted or simplified.

This embodiment is different from the above-mentioned embodiments in that a three-dimensional reconstruction unit 5 that uses multi-viewpoint images obtained in the second embodiment and three-dimensionally reconstructs the images is provided. The method of performing three-dimensional reconstruction is roughly divided into, for example, a method on the basis of multi-eye vision and a method on the basis of stereo vision. In this embodiment, the method on the basis of stereo vision, which is excellent in reproducibility of recessed portions on the cell surface, is adopted.

The three-dimensional reconstruction unit 5 includes an image database (DB) unit 51, a stereo image acquisition unit 52, a stereo matching unit 53, and a three-dimensional reconstruction database (DB) unit 54. Note that the three-dimensional reconstruction unit 5 may be configured as a part of the information processing apparatus 3. Further, the image DB unit 51 and the three-dimensional reconstruction DB unit 54 may be configured as separate devices from the three-dimensional reconstruction unit 5.

The image DB unit 51 stores cell images of multiple viewpoints acquired by the imaging unit 12. The stereo image acquisition unit 52 acquires two-viewpoint images among the cell images of multiple viewpoints acquired from the image DB unit 51, and acquires images obtained by collimating the optical axes of the two viewpoints. The stereo matching unit 53 performs stereo matching on the images of the two viewpoints with the collimated optical axes to obtain a three-dimensional image. The three-dimensional reconstruction DB unit 54 stores the image three-dimensionally reconstructed by the stereo matching unit 53.

Figure 13:
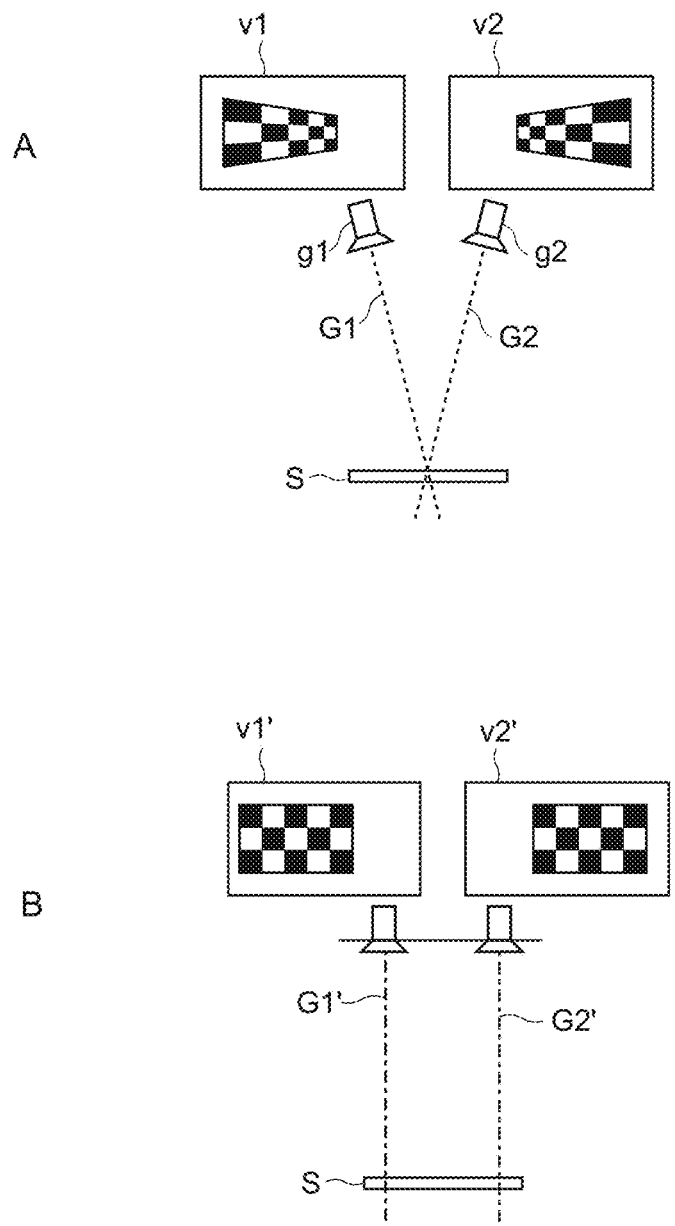
FIG. 13 is a diagram describing a general method of performing stereo matching from right and left images.

In general, in order to perform stereo matching, it is necessary to collimate the optical axes of right and left images. For example, in the case of imaging a sample S by cameras g1 and g2 with optical axes G1 and G2 not parallel to each other as shown in Part A of FIG. 13, images v1 and v2 acquired by the cameras g1 and g2 differ as shown in the figure. In this regard, as shown in Part B of FIG. 13, images v1' and v2' are generated by projective conversion so that optical axes G1' and G2' of the cameras g1 and g2 are parallel to each other. Note that the method of converting the optical axis is as described above.

Figure 14:
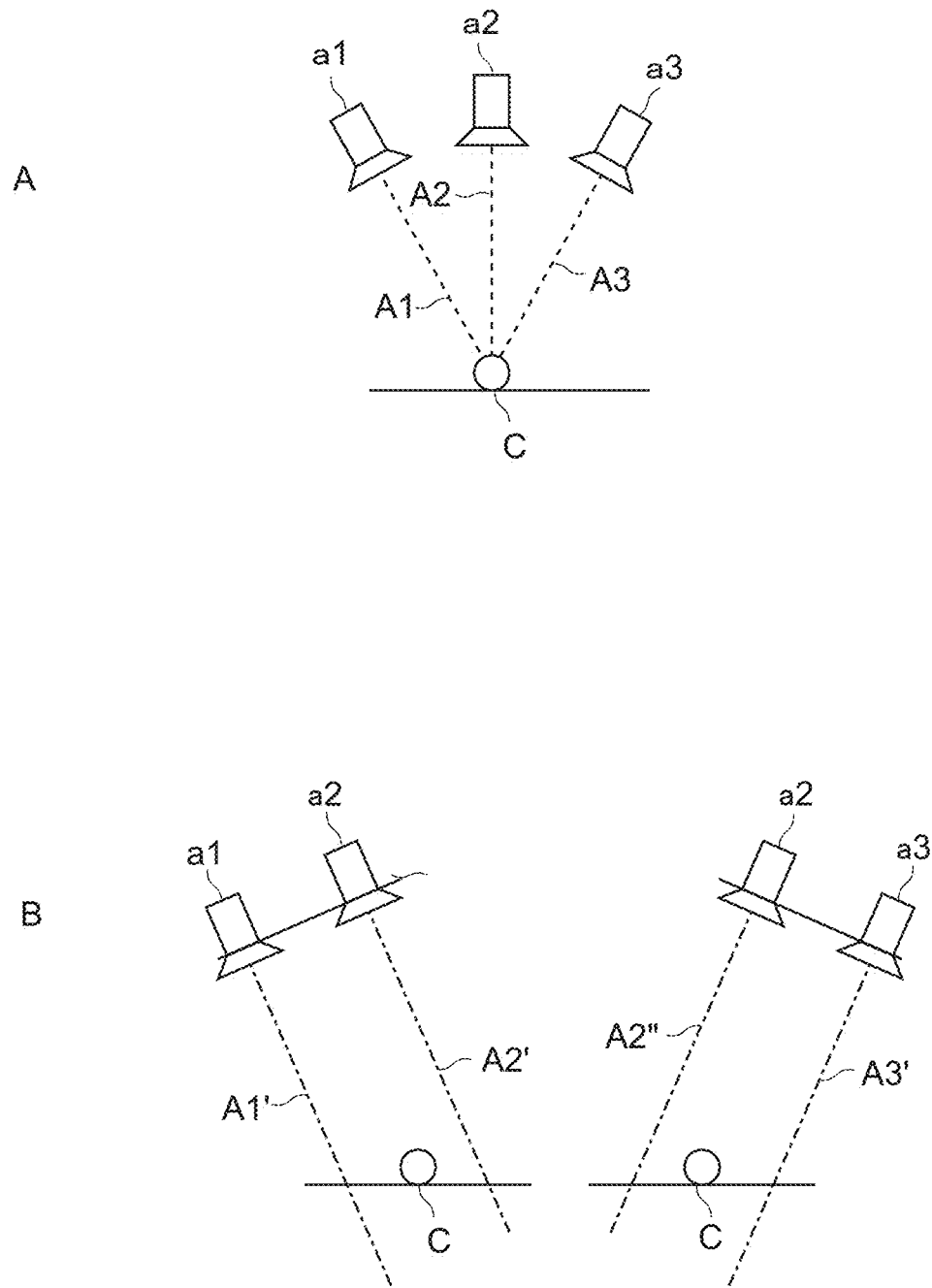
FIG. 14 is a diagram describing an example of the method of performing stereo matching from right and left images by the optical imaging unit (configuration example 1) in the observation system.

In addition, in the case where the cameras a1 to a3 are arranged along the circumferential direction of the upper hemisphere of the cell C as shown in Part A of FIG. 14 (see FIG. 5), in stereo matching processing, the optical axes may be collimated by the combination of the cameras a1 and a2 and the combination of the cameras a2 and a3 as shown in Part B of FIG. 14, for example. That is, the optical axes A1 and A2 and the optical axes A2 and A3 are collimated to generate images in which the optical axes are converted into optical axes A1' and A2' and optical axes A2" and A3', respectively.

Figure 15:
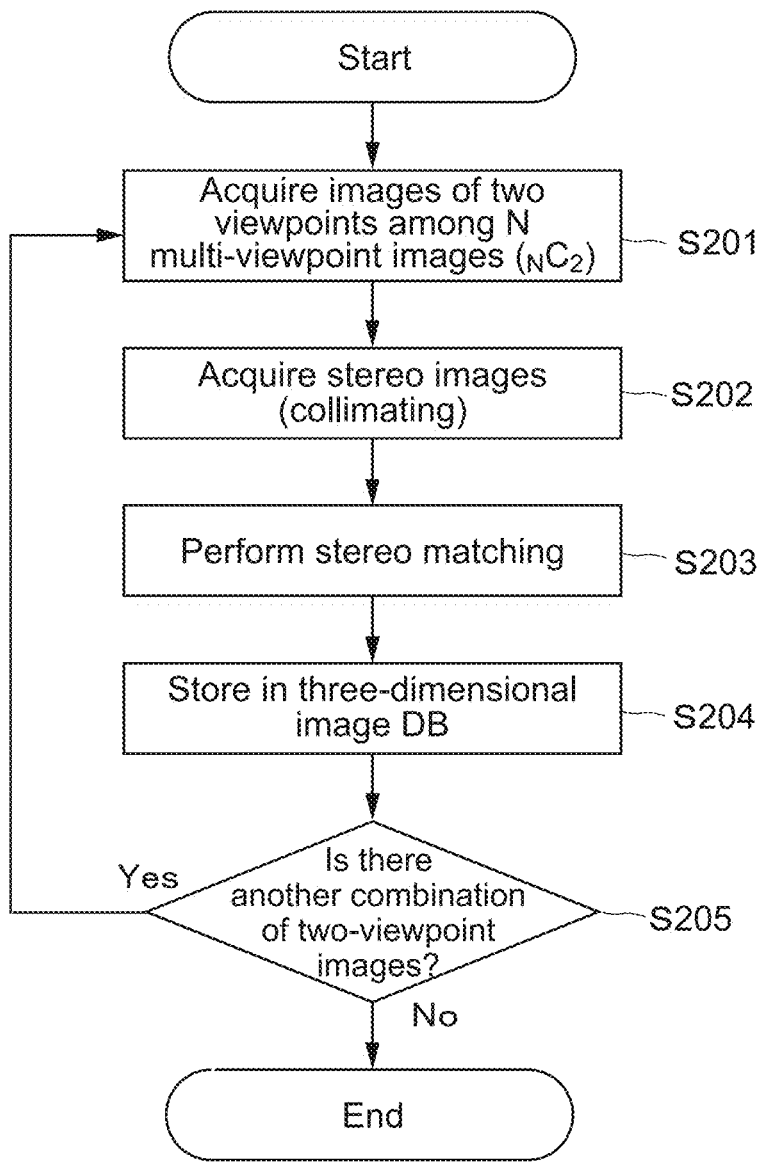
FIG. 15 is a diagram describing an operation example of a three-dimensional reconstruction unit according to a third embodiment of the present technology.
Figure 16:
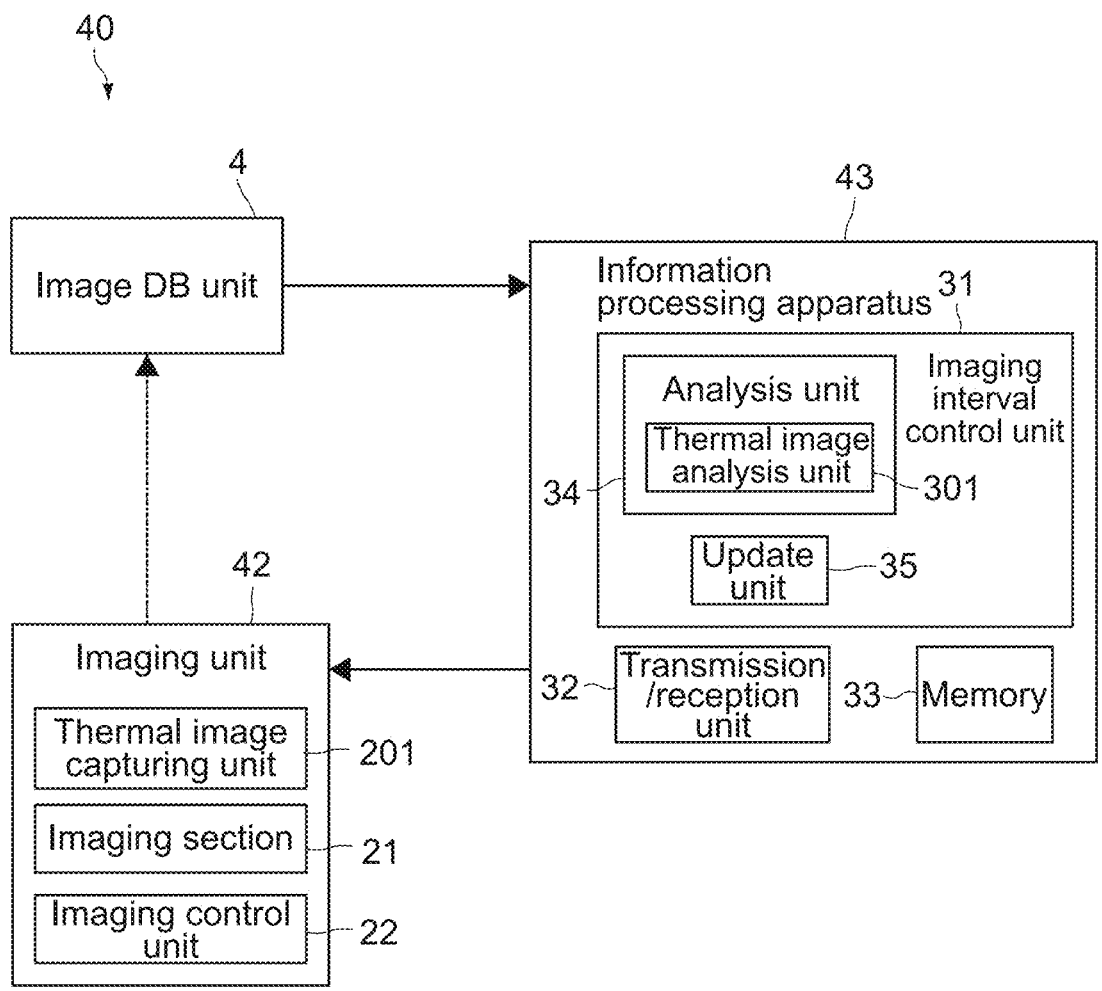
FIG. 16 is a block diagram showing a configuration of an observation system according to a fourth embodiment of the present technology.

FIG. 15 is a flowchart showing an operation example of the three-dimensional reconstruction unit 5.

The three-dimensional reconstruction unit 5 acquires combinations of images of two viewpoints among (N) cell images captured from a plurality of viewpoints first (S201). The three-dimensional reconstruction unit 5 creates stereo images by collimating the optical axes (S202) before creating a stereo matching image (S203) and storing the created three-dimensional image in the image DB unit 54 (S204). In the case where there is another combination of images of two viewpoints, a similar operation is repeated (S205). By performing stereo matching on all the combinations, it is possible to acquire a three-dimensional image of the cell.

The three-dimensional image created in this way is referred to for detecting the change in the state of the cell by the information processing apparatus 3. According to this embodiment, it is possible to precisely detect the change in the state of the cell, such as the unevenness of the surface and the change in the volume that it has not been able to detect by only the difference value between two-dimensional images.

Operation Example

The information processing apparatus 3 quantifies the features of the current cell image and the past cell image from the images stored in the three-dimensional reconstruction DB unit 54, and determines whether there is a change in the state of the cell on the basis of the change amount of the quantified feature amount. For example, in the case where the cell is a fertilized egg, the volume, the surface area, the sphericity, the degree of a surface irregularity of the fertilized egg, the uniformity of cleavage, and the like may be quantified, and the amount corresponding to the change may be reflected on the detection of whether there is a change in the state. Further, on the basis of movement of various feature points of the fertilized egg, it is possible to follow the movement that changes over time, such as rotation and movement of the cell in three-dimensional space. Accordingly, it is possible to precisely detect the change in the state of the cell, and adaptively switch the imaging interval in accordance with the change in the fertilized egg.

Fourth Embodiment

Next, a fourth embodiment of the present technology will be described. Hereinafter, configurations that are different from those according to the first embodiment will be mainly described. The configurations similar to those according to the first embodiment will be denoted by similar reference symbols and a description thereof will be omitted or simplified.

An observation system 40 according to this embodiment includes an imaging unit 42 and an information processing apparatus 43. This embodiment is different from the above-mentioned first embodiment in that the imaging unit 42 includes a thermal image capturing unit 201, and the information processing apparatus 43 includes a thermal image analysis unit 301.

The thermal image capturing unit 201 typically includes an infrared camera. The thermal image capturing unit 201 sequentially acquires a thermal image of the cell C in culture at a predetermined frame rate. The thermal image analysis unit 301 constitutes a part of the analysis unit 34, and is configured to constantly analyze the acquired thermal image of the cell C and detect whether there is a change in the state of the cell C in culture.

Note that the imaging unit 2 may include a single camera similarly to the first embodiment, or include a single camera or a plurality of cameras capable of acquiring multi-viewpoint images similarly to the second embodiment. Further, also the observation system 40 according to this embodiment may include the three-dimensional reconstruction unit 5 described in the third embodiment.

Figure 17:
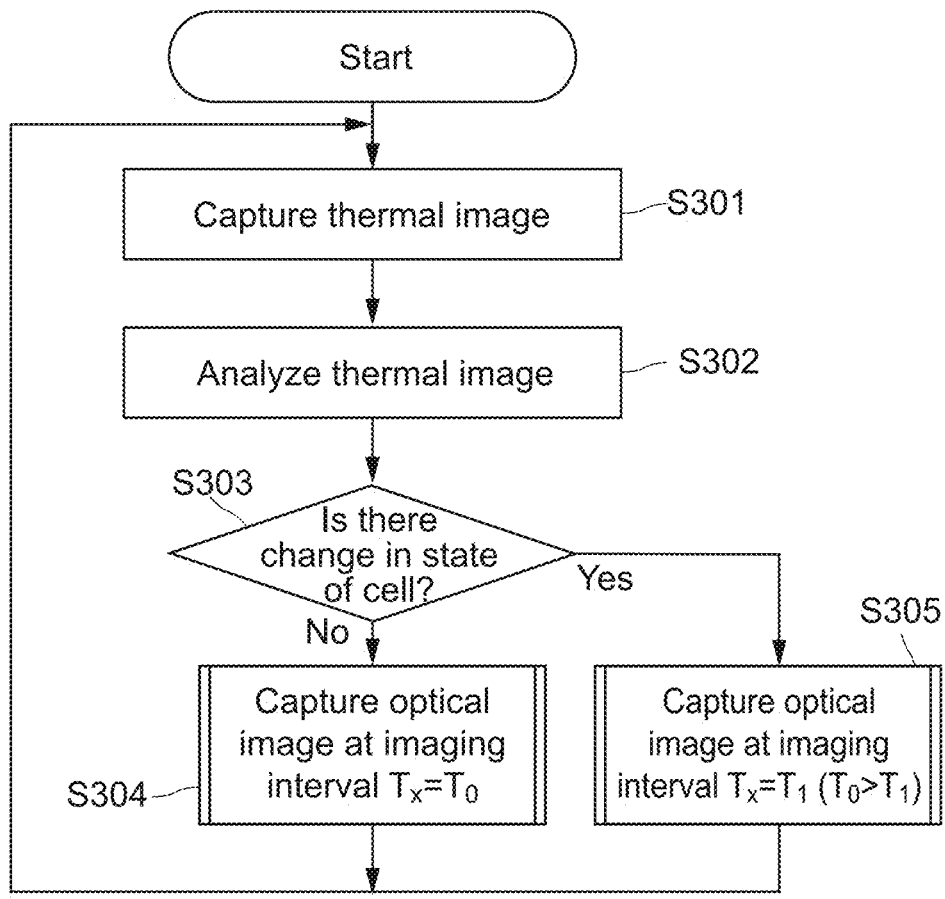
FIG. 17 is a flowchart describing an operation example of the observation system.

FIG. 17 is a flowchart showing a typical operation example of the observation system 40 according to this embodiment.

The observation system 40 according to this embodiment acquires, by the thermal image capturing unit 201, a thermal image of a cell (S301). Then, the information processing apparatus 43 analyzes the acquired thermal image (S302), and detects whether there is a change in the state of the cell C (S303). In the case where the change in the state of the cell C is not detected (No in S303), the information processing apparatus 43 maintains the imaging interval $T_0$ (initial set value) (S304). In the case where the change in the state of the cell is detected (Yes in S303), the information processing apparatus 43 switches the imaging interval from $T_0$ to $T_1$ shorter than $T_0$ (S305).

CONCLUSION

In the case of constantly imaging the change in the state of the cell by an optical imaging means, it is necessary to constantly apply light to the cell, which causes a great damage to the cell. According to this embodiment, by adopting a thermal image capturing means as a tool for detecting the change in the state of the cell instead of an optical imaging means, it is possible to constantly observe the change in the state while minimizing the damage on the cell. That is, since the change in the state of the cell can be detected even at the imaging interval where the optical imaging means does not image the cell, it is possible to acquire an optical image with less time lag in imaging at an important imaging timing related to cell evaluation.

In particular, since the thermal image capturing unit in this embodiment does not need a light source, it is possible to non-invasively image the cell. Therefore, it is suitable for constantly acquiring a cell image.

Although embodiments of the present technology have been described, it goes without saying that the present technology is not limited to only the above-mentioned embodiments and various modifications can be made.

It should be noted that the present technology may take the following configurations.

(1) An information processing apparatus, including:
a control unit that detects, on a basis of an optical image of a cell in culture captured at a first imaging interval, whether there is a change in a state of the cell, and switches, when detecting the change in the state, an imaging mode from the first imaging interval to a second imaging interval shorter than the first imaging interval.

(2) The information processing apparatus according to (1) above, in which
the control unit detects whether there is a change in the state of the cell from a thermal image of the cell in culture.

(3) The information processing apparatus according to (1) or (2) above, in which
the optical image is a three-dimensional image obtained from a plurality of optical images captured from multiple viewpoints, and
the control unit detects, depending on a change in a feature amount of the cell quantified on a basis of information of the three-dimensional image, whether there is a change in the state of the cell.

(4) The information processing apparatus according to any one of (1) to (3) above, in which
the cell is a fertilized egg, and
the feature amount of the cell is a volume, a surface area, a sphericity, and a degree of a surface irregularity of the fertilized egg, and a uniformity of cleavage.

(5) An observation system, including:
a cell culture vessel that cultures a cell;
an imaging unit that includes an optical image capturing unit acquiring, at a first interval, an optical image of the cell in culture; and
a control unit detects, on a basis of an image of the cell in culture captured at the first imaging interval, whether there is a change in a state of the cell, and switches, when detecting the change in the state, an imaging mode from the first imaging interval to a second imaging interval shorter than the first imaging interval.

(6) The observation system according to (5) above, in which
the imaging unit includes a thermal image capturing unit sequentially acquiring a thermal image of the cell in culture, and
the control unit detects, on a basis of the thermal image captured by the thermal image capturing unit, whether there is a change in the state of the cell.

(7) The observation system according to (5) or (6) above, in which
the optical image capturing unit acquires multi-viewpoint optical images of the cell, the observation system further including:
an optical image database unit that stores the multi-viewpoint optical images; and
a three-dimensional reconstruction unit that acquires the multi-viewpoint optical images from the optical image database unit, and three-dimensionally reconstructs the multi-viewpoint optical images.

(8) The observation system according to (7) above, in which
the control unit detects, on a basis of the three-dimensionally reconstructed multi-viewpoint optical images, whether there is a change in the state of the cell.

(9) An observation method, including:
detecting, on a basis of an optical image of a cell in culture captured at a first imaging interval, whether there is a change in a state of the cell; and
switching, when detecting the change in the state, an imaging mode from the first imaging interval to a second imaging interval shorter than the first imaging interval.

(10) A program that causes an information processing apparatus to execute the steps of:
detecting, on a basis of an optical image of a cell in culture captured at a first imaging interval, whether there is a change in a state of the cell; and
switching, when detecting the change in the state, an imaging mode from the first imaging interval to a second imaging interval shorter than the first imaging interval.

REFERENCE SIGNS LIST

1, 11, 12 culture vessel
2, 12, 42 imaging unit 3, 43 information processing apparatus
4, 51 image DB unit
5 three-dimensional reconstruction unit
10, 20, 30, 40 observation system
11 cylindrical vessel
14 analysis unit
15 update unit
31 imaging interval control unit
32 transmission/reception unit
33 memory
34 analysis unit
30, 40 observation system
52 stereo image acquisition unit
53 stereo matching unit
54 three-dimensional reconstruction DB unit
201 thermal image capturing unit
301 thermal image analysis unit
a1 to a3, b1, d1 to d3, f1 to f3, g1 to g2 camera
M1 to M3 mirror

The invention claimed is:

1. An information processing apparatus including a processor, comprising:
a controller configured to detect, on a basis of an image of a fertilized egg in culture captured at a first imaging interval, whether there is a change in a state of the fertilized egg, and switches, when detecting the change in the state, an imaging mode from the first imaging interval to a second imaging interval shorter than the first imaging interval; wherein
the image is a three-dimensional image obtained from a plurality of images captured from multiple viewpoints, and
the controller detects, depending on a change in a feature amount of the fertilized egg quantified on a basis of information of the three-dimensional image, whether there is a change in the state of the fertilized egg; wherein
the feature amount of the fertilized egg is at least one of a sphericity, a degree of a surface irregularity of the fertilized egg, and a uniformity of cleavage.

2. The information processing apparatus according to claim 1, wherein
the controller detects whether there is a change in the state of the fertilized egg from a thermal image of the fertilized egg in culture.

3. An observation system including a processor, comprising:
an imaging device that includes an optical imager configured to acquire, at a first interval, an image of a fertilized egg in culture; and
a controller configured to detect, on a basis of an image of the fertilized egg in culture captured at the first imaging interval, whether there is a change in a state of the fertilized egg, and switches, when detecting the change in the state, an imaging mode from the first imaging interval to a second imaging interval shorter than the first imaging interval; wherein
the optical image is a three-dimensional image obtained from a plurality of images captured from multiple viewpoints, and
the controller detects, depending on a change in a feature amount of the fertilized egg quantified on a basis of information of the three-dimensional image, whether there is a change in the state of the fertilized egg; wherein
the feature amount of the fertilized egg is at least one of a sphericity, a degree of a surface irregularity of the fertilized egg, and a uniformity of cleavage.

4. The observation system according to claim 3, wherein
the imager includes a thermal imager configured to sequentially acquire a thermal image of the cell in culture, and
the controller detects, on a basis of the thermal image captured by the thermal imager, whether there is a change in the state of the fertilized egg.

5. The observation system according to claim 3, wherein
the optical imager acquires multi-viewpoint optical images of the fertilized egg, the observation system further comprising:
an optical image database that stores the multi-viewpoint optical images; and
a three-dimensional reconstructor that acquires the multi-viewpoint optical images from the optical image database unit, and three-dimensionally reconstructs the multi-viewpoint optical images.

6. The observation system according to claim 5, wherein
the controller detects, on a basis of the three-dimensionally reconstructed multi-viewpoint optical images, whether there is a change in the state of the fertilized egg.

7. An observation method, comprising:
detecting, on a basis of an image of a fertilized egg in culture captured at a first imaging interval, whether there is a change in a state of the fertilized egg; and
switching, when detecting the change in the state, an imaging mode from the first imaging interval to a second imaging interval shorter than the first imaging interval; wherein
the image is a three-dimensional image obtained from a plurality of images captured from multiple viewpoints, and
the controller detects, depending on a change in a feature amount of the fertilized egg quantified on a basis of information of the three-dimensional image, whether there is a change in the state of the fertilized egg; wherein
the feature amount of the fertilized egg is at least one of a sphericity, a degree of a surface irregularity of the fertilized egg, and a uniformity of cleavage.

8. A non-transitory computer readable storage medium having computer readable instructions stored thereon that, when executed by a processor in an information processing apparatus, cause the information processing apparatus to execute the steps of:
detecting, on a basis of an image of a fertilized egg in culture captured at a first imaging interval, whether there is a change in a state of the fertilized egg; and
switching, when detecting the change in the state, an imaging mode from the first imaging interval to a second imaging interval shorter than the first imaging interval; wherein
the image is a three-dimensional image obtained from a plurality of images captured from multiple viewpoints, and
the controller detects, depending on a change in a feature amount of the fertilized egg quantified on a basis of information of the three-dimensional image, whether there is a change in the state of the fertilized egg; wherein the feature amount of the fertilized egg is at least one of a sphericity, a degree of a surface irregularity of the fertilized egg, and a uniformity of cleavage.

\* \* \* \* \*